United States Patent [19]
Uhlmann et al.

[11] Patent Number: 6,037,463
[45] Date of Patent: Mar. 14, 2000

[54] ENZYMATIC RNA MOLECULES THAT CLEAVE MUTANT N-RAS

[75] Inventors: Eugen Uhlmann, Glashuetten; Joachim Engels, Kronberg; Michaela Scherr, Oberursel; Arnold Ganser, Hannover, all of Germany

[73] Assignee: Hoechst Aktiengesellschaft, Frankfurt, am Main, Germany

[21] Appl. No.: 08/862,270

[22] Filed: May 23, 1997

[30] Foreign Application Priority Data

May 24, 1996 [EP] European Pat. Off. .............. 96108326

[51] Int. Cl.[7] .................................................. C07H 21/00
[52] U.S. Cl. .............................. 536/24.5; 435/6; 435/375
[58] Field of Search .......................... 435/6, 91.3, 91.31, 435/172.1, 320.1, 325, 375; 514/44; 536/24.5; 935/33, 34, 36, 44

[56] References Cited

U.S. PATENT DOCUMENTS 4,871,838  10/1989  Bos et al. .............................. 536/24.31

FOREIGN PATENT DOCUMENTS

| 0 552 766 | 7/1993 | European Pat. Off. . |
| 0 593 901 | 4/1994 | European Pat. Off. . |
| 0 672 677 | 9/1995 | European Pat. Off. . |
| 91/18625 | 12/1991 | WIPO . |
| 91/18913 | 12/1991 | WIPO . |
| 92/07065 | 4/1992 | WIPO . |
| 93/23057 | 11/1993 | WIPO . |

OTHER PUBLICATIONS

Antisense '97: A roundtable on the state of the industry. Nature Biotechnol. 15: 519–524, Jun. 1997.

Burke. Clearing the way for ribozymes. Nature Biotechnol. 15: 414–415, May 1997.

Gewirtz et al. Facilitating oligonucleotide delivery: Helping antisense deliver on its promise. Proc. Natl. Acad. Sci. USA. 93: 3161–3163, Apr. 1996.

Rojanasakul. Antisense oligonucelotide therapeutics: Drug delivery and targeting. Adv. Drug Delivery Rev. 18: 115–131, 1996.

D.M. Williams et al., "Function of specific 2'–hydroxyl Groups of Guanosines in a Hammerhead ribozyme Probe by 2' Modifications", Proc. Natl. Acad. Sci. USA, vol. 80, 1992, pp. 918–921.

J. Yang et al., "Minimum Ribonucleotide Requirement for Catalysis by the RNA Hammerhead Domain", Biochemistry, vol. 31, No. 21, 1992, pp. 5005–5009.

N. Taylor et al., "Chimeric DNA–RNA Hammerhead Ribozymes Have Enhanced in vitro Catalytic Efficiency and Increased Stability in vivo", Nucleic Acids Research, vol. 20, No. 17, 1992, pp. 4559–4565.

R.A. Stull et al., "Antigene, Ribozyme and Aptamer Nucleic Acid Drugs: Progress and Prospects", Pharmaceutical Review, vol. 12, No. 4, 1995, pp. 465–483.

T. Shimayama et al., "Nuclease–resistant Chimeric Ribozymes Containing Deoxyribonucleotides and Phosphorothioate Linkages", Nucleic Acids Research, vol. 21, No. 11, 1993, pp. 2605–2611.

S. Shibahara et al., "Inhibition of Human Immunodeficiency Virus (HIV–1) Replication by Synthetic Oligo–RNA Derivatives", Nucleic Acids Research, vol. 17, No. 1, 1989, pp. 239–253.

M. Portier et al., "p53 and RAS Gene Mutations in Multiple Meyloma", Oncogene, vol. 7, 1992, pp. 2539–2543.

G. Paolella et al., "Nuclease Resistant Ribozymes with High Catalytic Activity", The EMBO Journal, vol. 11, No. 5 1992, pp. 1913–1919.

D.B. Olsen et al., "Study of a Hammerhead Ribozyme Containing 2'–Modified Adenosine Residues", Biochemistry, vol. 30, No. 40, 1991, pp. 9735–9741.

K.J. Hertel et al., "Numbering System for the Hammerhead", Nucleic Acids Research, vol. 20, No. 12, 1992.

O. Heidenreich et al., "Hammerhead Ribozyme–mediated Cleavage of the Long Terminal Repeat RNA of Human Immunodeficiency Virus Type 1", Journal of Biol. Chem., vol. 267, No. 3, 1992, pp. 1904–1909.

O. Heidenreich et al., "High Activity and Stability of Hammerhead Ribozymes Containing 2'–Modified Pyrimidine Nucleosides and Phosphorothioates", J. of Biol. Chem., vol. 269, No. 3, 1994, pp. 2131–2138.

J. Goodchild, "Enhancement of Ribozyme Catalytic Activity by a Contiguous Oligodeoxynucleotide (facilitator) and by 2'–O–methylation", Nucleic Acids Research, vol., 20, No. 17, 1992, pp. 4607–4612.

D. Fu et al., "Importance of Specific Purine Amino and Hydroxyl Groups for Efficient Cleavage by a Hammerhead Ribozyme", Proc. Natl. Acad. Sci. USA, vol. 89, 1992, pp. 3985–3989.

S.C. Dahm et al., "Role of Divalent Metal Ions in the Hammerhead RNA Cleavage Reaction", Biochemistry, vol. 30, No. 39, 1991, pp. 9464–9469.

J.L. Bos, "ras Oncogenes in Human Cancer: A Review", Cancer Research, vol. 49, 1989, pp. 4682–4689.

L. Beigelman et al., "Chemical Modification of Hammerhead Ribozymes", J. of Biol. Chem., vol. 270, No. 43, 1995, pp. 25702–25708.

(List continued on next page.)

*Primary Examiner*—John S. Brusca
*Assistant Examiner*—Thomas G. Larson
*Attorney, Agent, or Firm*—Foley & Lardner

[57] ABSTRACT

Enzymatic RNA molecules have been designed that cleave mutant N-ras mRNA, preferably at a NUX cleavage site (N=any base, X=A, C or U). Preferred ribozymes have nucleotide sequences 5'-CCAACACCUGAUGAGCGUUAGCGAAACCUGCU-3' or 5'-UCCCAACCUGAUGAGCGUUAGCGAAACACCUG-3' (SEQ ID NOS:1 and 2), and derivatives thereof. The present invention also provides pharmaceuticals containing such molecules and the use of such molecules for the preparation of pharmaceuticals for the treatment of diseases involving abnormal cell growth and/or differentiation.

23 Claims, 2 Drawing Sheets

OTHER PUBLICATIONS

S. Beaucage et al., "The Synthesis of Modified Oligonucleotides by the Phosphoramidite Approach and their Applications", vol. 49, No. 28, 1993, pp. 6123–6194.

S. Beaucage et al., "The Functionalization of Oligonucleotides Via Phosphoramidite Derivatives", Tetraheadron, vol. 49, No. 10, 1993, pp. 1925–1963.

J. Haseloff et al., Simple RNA Enzymes with New and Highly Specific Endoribonuclease Activities, Nature, vol. 334, 1988, pp. 585–591.

M. Koizumi et al., "Ribozymes Designed to Inhibit Transformation of NIH3T3 Cells by the Activated c–Ha–ras Gene", Gene 117 (1992) pp. 179–184.

R. Perriman et al., "Extended Target–site Specificity for a Hammerhead Ribozyme", Gene, 113 (1992), pp. 157–163.

P. Stephenson et al., "In Vitro Cleavage of an N–ras Messenger–Like RNA by a Ribozyme", Antisense Research and Development, (1991), pp. 261–268.

A. Cleve et al., "Synthesis of Oxygen–Bridged Antigestagens", Tetrahedron, vol. 49, No. 11, (1993), p. 2217–2226.

Francis A. Waldvogel, "*Staphylococcus Aureus* (Including Toxic Shock Syndrome)", *Infectious Diseases and Their Etiologic Agents*, Part III, pp. 1754–1777.

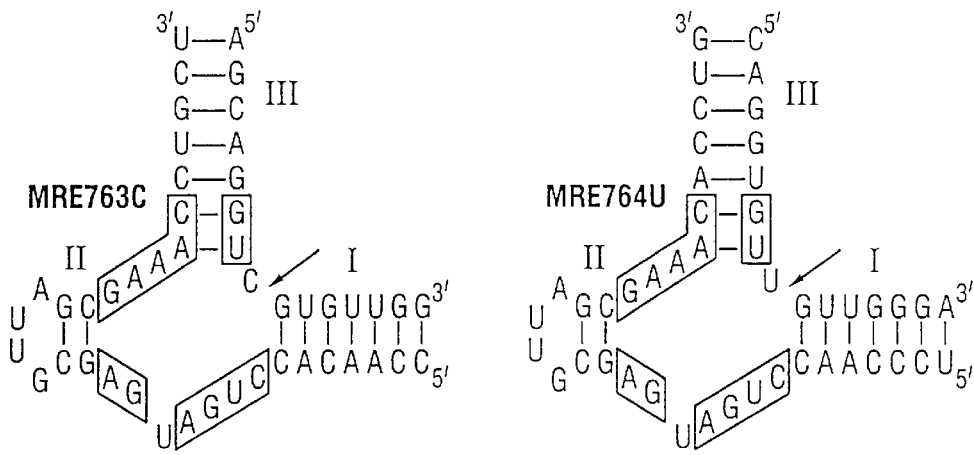
Fig. 1(A): Design of chemically synthesized hammerhead ribozymes.
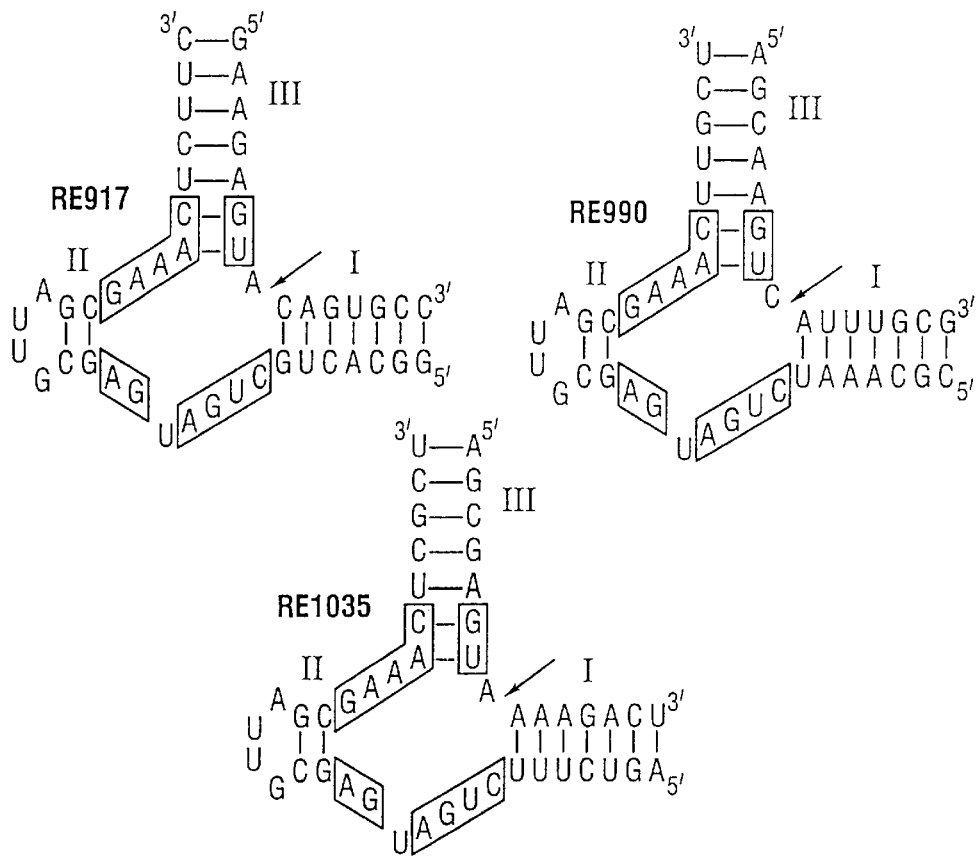
Fig. 1(B): Design of chemically synthesized hammerhead ribozymes.

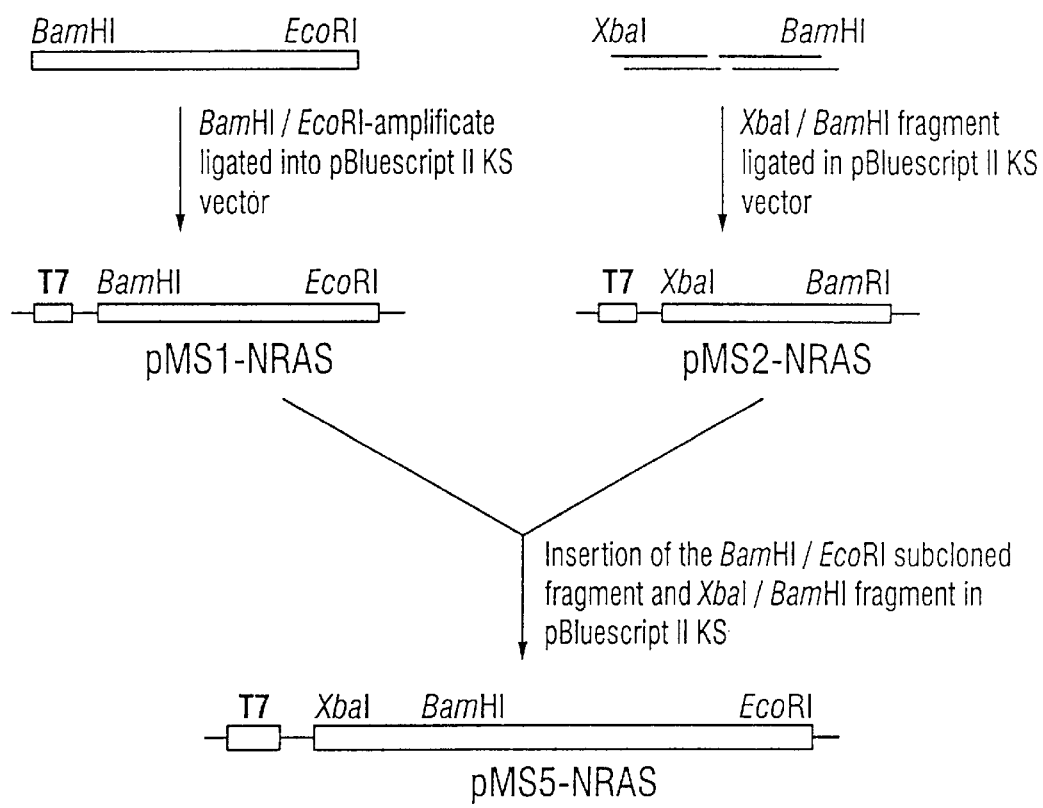
Fig. 2: Cloning strategy of the plasmid pMS5-NRAS.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:1:

CCAACACCUG AUGAGCGUUA GCGAAACCUG CU    32

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:2:

UCCCAACCUG AUGAGCGUUA GCGAAACACC UG    32

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:3:

AGTGCGGATC CTAAATCTGT CCAAAGCAGA GGCAGT    36

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:4:

CCGGAATTCT TACATCACCA CACATGGCAA TCC    33

(2) INFORMATION FOR SEQ ID NO:5:

(i) SEQUENCE CHARACTERISTICS:
        (A) LENGTH: 100 base pairs
        (B) TYPE: nucleic acid (C) STRANDEDNESS: single
            (D) TOPOLOGY: linear (xi) SEQUENCE DESCRIPTION: SEQ ID NO:5:

CTAGAGAAAC GTCCCGTGTG GGAGGGGCGG GTCTGGGTGC GGCTGCCGCA TGACTCGTGG      60

TTCGGAGGCC CACGTGGCCG GGGCGGGGAC TCAGGCGCCT                           100

(2) INFORMATION FOR SEQ ID NO:6:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (xi) SEQUENCE DESCRIPTION: SEQ ID NO:6:

GCTGCCAGGC GCCTGAGTCC CCGCCCCGGC CACGTGGGCC TCCGAACCAC GAGTCATGCG      60

GCAGCCGCAC CCAGACCCGC CCCTCCCACA CGGGACGTTT CT                       102

(2) INFORMATION FOR SEQ ID NO:7:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (xi) SEQUENCE DESCRIPTION: SEQ ID NO:7:

GGCAGCCGAC TGATTACGTA GCGGGCGGGG CCGGAAGTGC CGCTCCTTGG TGGGGGCTGT      60

TCATGGCGGT TCCGGGGTCT CCAACATTTT TCCCGGTCTG G                        101

(2) INFORMATION FOR SEQ ID NO:8:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (xi) SEQUENCE DESCRIPTION: SEQ ID NO:8:

GATCCCAGAC CGGGAAAAAT GTTGGAGACC CCGGAACCGC CATGAACAGC CCCCACCAAG      60

GAGCGGCACT TCCGGCCCCG CCCGCTACGT AATCAGTCG                            99

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:9:

GCAGGTGTTG TTGGGAAAAG CGCACTG                                         27

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

CAACAACACC TGCTCCAACC ACCAC                                           25

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:11:

GCAGGTCGTG TTGGGAAAAG CGCACTG                                  27

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

CCCAACACGA CCTGCTCCAA CCACCAC                                  27

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:13:

AGTGCTCTAG AGAAACGTCC CGTGTGGGAG GGGCG                            35

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

GGCACUGCUG AUGAGCGUUA GCUAAACUCU UC                                32

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:15:

CGCAAAUCUG AUGAGCGUUA GCGAAACUUG CU                                32

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:16:

AGUCUUUCUG AUGAGCGUUA GCGAAACUCG CU                                32

ENZYMATIC RNA MOLECULES THAT CLEAVE MUTANT N-RAS

BACKGROUND OF THE INVENTION

1. Field of the Invention

The invention relates to enzymatic RNA molecules which cleave mutant N-ras mRNA, preferably at a NUX cleavage site (N=any base, X=A, C or U), pharmaceuticals containing such molecules and use of such molecules for the preparation of pharmaceuticals for the treatment of diseases involving abnormal cell growth and/or differentiation.

2. Related Art

The growth and differentiation of cells depends on a variety of parameters and signal pathways. The inhibition of expression of certain signal transduction proteins may lead to an efficient therapy. Three ras-genes (Ha-ras, N-ras, Ki-ras) coding for ras-proteins are essentially involved in cell signal transduction and are members of the super gene family of small GTP/GDP binding proteins.

Studies of ras-oncogenes in tumors revealed point mutations leading to amino acid substitutions. Point mutations in the codons 12, 13, 59 and 61 cause structural changes of the GTP binding site and a reduced GTPase activity. Ras mutations have been detected in a wide variety of tumors such as pancreatic carcinomas, tumors in stomach and breast. Bos, *Cancer Research* 49:4682 (1989). N-ras mutations have been found in neuroblastoma, melanoma, acute myeloblastic leukaemia (AML), chronic myelogenous leukaemia (CML) and multiple myeloma. Portier et al., *Oncogene* 7:2539 (1992).

Enzymatic RNA molecules include Group I- and Group II-introns: Hammerhead ribozymes, hairpin ribozymes, hepatitis delta virus ribozymes ("axehead"), self-splicing introns and the subunit of RNAse P. Ribozymes of the hammerhead type are the smallest catalytic RNA ever found. Hammerhead ribozymes consist of three stems and 11 of 13 conserved nucleotides. They contain a consensus sequence which is part of the hammerhead structure. They recognize substrates containing NUX base triplet (N can be any base; X can be A, C, or U) and cleave the phosphodiester bond on the 3' side of X in trans position specifically. The GUC base triplet is cleaved most efficiently. Dahm et al., Biochemistry 30:9464 (1991).

Enzymatic RNA molecules which specifically cleave mRNA have been described previously (WO93/23057). Although enzymatic cleavage of ras mRNA has been mentioned in this application, it has not been disclosed which type of ras gene (Ha-ras, Ki-ras or N-ras) can be cleaved, and more importantly, it has not been shown which region within the ras mRNA sequence could be cleaved. Furthermore, only wild-type ras gene has been suggested as target, but no mutant ras genes.

In another application (WO 91/18913), ribozymes which cleave Ha-ras mRNA at codon 12 were described. However, the described ribozymes would not allow cleavage of other ras types such as N-ras. The described ribozymes are also not stable under in vivo conditions.

Therefore, enzymatic RNA molecules that cleave mutant N-ras mRNA have potential as therapeutic agents, but a need exists for ribozymes that cleave mutant N-ras mRNA in predictable manner.

SUMMARY OF THE INVENTION

Accordingly, it is an object of the present invention to provide enzymatic RNA molecules that are targeted against mutant mRNA, but do not cleave wild type N-ras mRNA. Such ribozymes can inhibit the expression of the N-ras oncogene without inhibiting the expression of the N-ras proto-oncogene.

Another object of this invention is to provide ribozymes that are designed to cleave mutant N-ras mRNA, and that are stable in vivo.

These and other objects are achieved, in accordance with one embodiment of the present invention by an enzymatic RNA molecule that cleaves mutant N-ras mRNA, wherein the enzymatic RNA molecule comprises a region that binds mutant N-ras.

The present invention also contemplates an enzymatic RNA molecule that cleaves mutant N-ras mRNA at a NUX cleavage site, where N can be any base and X can be A, C or U.

In addition, the present invention is directed to an enzymatic RNA molecule consisting of 13 to 50 nucleotides, wherein the enzymatic RNA molecule cleaves mutant N-ras mRNA at a NUX cleavage site, where N can be any base and X can be A, C or U.

The present invention further contemplates a pharmaceutical composition comprising (1) at least one enzymatic RNA molecule that cleaves mutant N-ras mRNA, and (2) a pharmaceutically acceptable vehicle.

The present invention also is directed to a method for treating a disease that is caused by or associated with the expression of mutant N-ras, the method comprising the administration of a therapeutically effective amount of a pharmaceutical composition comprising at least one enzymatic RNA molecule that cleaves mutant N-ras mRNA to a subject in need of such treatment. Examples of such diseases include neuroblastoma, melanoma, acute myeloblastic leukaemia, chronic myelogenous leukaemia, multiple myeloma, thyroid tumor, lymphoid disorder and liver carcinoma.

BRIEF DESCRIPTION OF THE DRAWINGS

FIG. 1A and FIG. 1B illustrate the design of chemically synthesized hammerhead ribozymes. Panel A shows ribozymes which are targeted against mutant N-ras mRNA. Panel B shows ribozymes which are targeted against the wild-type N-ras mRNA. The cleavage site is indicated by an arrow and the consensus sequences are boxed. Stems are numbered according to Hertel et al., *Nucl. Acids Res.* 20:3252 (1992).

FIG. 2 presents the cloning strategy for the plasmid pMS5-Nras. The pcN1 amplificate and 200 bp fragment were separately ligated in PBLUESCRIPT II KS. In a three-part ligation both fragments were ligated behind the T7 promoter in the PBLUESCRIPT transcription vector.

DETAILED DESCRIPTION

The present invention describes the use of enzymatic RNA molecules, especially hammerhead ribozymes, which are targeted against N-ras mRNA. The enzymatic RNA molecules of this invention are directed against mutant N-ras mRNA which cleave the mutant N-ras mRNA, preferably after codon 13. Cleavage at codon 13 has not been achieved previously for any of the ras mRNA's. Surprisingly, enzymatic RNA molecules could be obtained which are stable under in vivo conditions and which selectively cleave at codon 13 of mutant N-ras mRNA. In particular, the invention features enzymatic RNA molecules which cleave the mutant N-ras mRNA at a NUX cleavage site, where N can be any base and X can be A, C or U.

Preferred are enzymatic RNA molecules consisting of 13 to 50 nucleotides which are able to cleave mutant N-ras mRNA at a NUX cleavage site, where N can be any base and X can be A, C or U. Particularly preferred are enzymatic RNA molecules where this RNA features a hammerhead motif.

Particular mention is made furthermore of enzymatic RNA molecules where the RNA is modified as a nuclease-resistant moiety. Preferred enzymatic molecules have modifications at the internucleoside phosphate residue and/or at the 2'-position of the ribose unit of nucleotides. Particularly preferred modifications at this 2'-position are 2'-amino and 2'-fluoro groups.

Especially preferred ribozymes have the base sequence 5'-CCAACACCUGAUGAGCGUUAGCGAAACCUGCU-3' ("MRE763C"; SEQ ID NO:1), or 5'-UCCCAACCUGAUGAGCGUUAGCGAAACACCUG-3' ("MRE764U"; SEQ ID NO:2).

The invention also relates to a pharmaceutical compositions containing one or more of the enzymatic RNA molecules, where appropriate together with physiologically tolerated ancillary substances and/or vehicles. Preferred vehicles are liposomes, immuno liposomes, microparticles and nanoparticles. Furthermore, the invention relates to the use of such molecules for the preparation of pharmaceuticals for the treatment of diseases which are caused by or associated with the expression of N-ras involving abnormal cell growth and/or differentiation.

An "enzymatic RNA molecule" is a nucleic acid or a nucleic acid analog which binds in a predictable way to a specific region on the target mRNA and which is able to cleave that mRNA at a predictable site. Enzymatic RNA molecules include Group I- and Group II-introns: Hammerhead ribozymes, hairpin ribozymes, hepatitis delta virus ribozymes ("axehead"), self-splicing introns and the subunit of RNAse P. Preferred ribozymes of these invention are those of the hammerhead type.

Ribozymes can be delivered in an exogenous or endogenous way into cells. "Exogenous" means that chemically synthesized ribozymes or in vitro transcripts, produced with T7 RNA polymerase, are applied directly to cells. The endogenous method requires a plasmid or viral vector that produces the corresponding ribozyme via gene expression. Both types of ribozymes, synthetic or vector-encoded, are within the scope of this invention.

The problem that arises from exogenous delivery is the low stability of ribozymes due to degradation by nucleases occurring in cell culture supernatant. Since the 2'-hydroxy group plays an important role in the degradation mechanism by nucleases, RNA can be stabilized by 2'-modifications. Therefore, 2'-desoxyribonucleotides, 2'-O-methylgroups, 2'-fluoro- and/or 2'-aminogroups or 2'-desoxyribonucleotides together with phosphorothioat linkages were introduced. Tayler et al., *Nucleic Acids Res.* 20:4559 (1992); Yang et al., *Biochemistry* 31:5005 (1992); Goodchild, *Nucleic Acids Res.* 20:4607 (1992); Heidenreich et al., *J. Biol. Chem.* 269:2131 (1994); Shibahara et al., *Nucleic Acids Res.* 17:239 (1989).

Basically, any chemical modification can be introduced to ribozymes of the present invention which results in generic, catalytically active ribozymes. Beigelman et al., *J. Biol. Chem.* 270:25702 (1995); Shimayama et al., *Nucleic Acids Res.* 21:2606 (1993); Dong-Jing Fu et al., *Proc. Nat'l Acad. Sci.* 89:3985 (1992); Olsen et al., *Biochemistry* 30:9735 (1991); Williams et al., *Proc. Nat'l Acad. Sci.* 89:918 (1992); Paolella et al., *The EMBO Journal* 11:1913 (1992).

Ribozymes can be chemically synthesized employing known methods. See, for example, Gait, "OLIGONUCLEOTIDE SYNTHESIS—A PRACTICAL APPROACH (IRL Press, 1984); Beaucage et al., *Tetrahedron* 49: 1925 & 2223 & 6123 (1993); Uhlmann et al., *Chemical Reviews* 90:543 (1990); EP-A 0 552 766; EP-A 0 593 901; and references for modifications above. The construction of vector-encoded ribozymes has been described previously. Stull et al., *Pharmaceutical Research* 12:465 (1995); Murray (Ed.) in "ANTISENSE RNA AND DNA, (Wiley-Liss, Inc., 1992); Baserga et al., (Eds.) in "ANNALS OF THE NEW YORK ACADEMY OF SCIENCES—ANTISENSE STRATEGIES, Vol. 660 (The New York Academy of Sciences, 1992).

The invention is not confined to natural L-ribofuranoside or phosphates unit in the backbone, or to the natural bases in the recognition part. Any modification in the backbone, the sugar or bases is within the scope of this invention as long as the enzymatic cleavage activity is retained. Modifications of the sugar include alpha- and D-furanosides, carbocyclic five-membered ring analogs, ring-expanded and ring-contracted sugars, and acyclic sugars. These modifications are preferably in the binding region of the ribozyme. The sugar may be modified as 2'-O-alkylribose such as 2'-O-methyl, 2'-O-butyl, 2'-O-allyl, 2'-O-methoxyethoxy, or as 2'-fluoro-2'-deoxyribose, 2'-amino-2'deoxyribose. Modifications of the phosphate internucleoside residue include phosphorothioates, phosphorodithioates, alkylphosphonates, arylphosphonates, arylalkylphosphoramidates, phosphate esters, or combinations of these modifications with phosphodiesters or themselves. The phosphate bridge may also be replaced by formacetal, 3'-thioformacetal, and methylhydroxylamine. Modifications of the bases include 5-propynyl-U, 5-propynyl-C, 7-deaza-7-propynyl-A, 7-deaza-7-propynyl-G, 5-methyl-C, 5-fluoro-U, where the base is a ribo- or deoxyribonucleotide Very preferred phosphate modifications are 3'3' or 5'5'-inversions as described in EP-A 0 593 901. Partial substitution of the phosphate/sugar backbone by polyamide nucleic acids as described in EP-A 0 672 677 is also a preferred embodiment of this invention.

Preferred are also end-group modifications at either the 5'- or 3'(2')-terminus as described in EP-A 0 552 766. Examples of end-modifications are lipophilic radicals such as —O—(CH$_2$)$_n$CH$_3$ (n=6 to 18), or steroid residues, or vitamins E, A or D, or conjugates which utilize natural carrier systems such as bile acid, folic acid, mannose, or peptides. Other end-groups are intercalating moieties which enhance binding to the target such as psoralene and acridine derivatives.

It has to be remarked that all modifications discussed above may occur once or more in a certain RNA-molecule and that the modifications can be combined to obtain extremely stable and biologically active ribozymes.

In order to inhibit expression of mutant N-ras, different ribozymes against codon 13 of mutant N-ras mRNA where synthesized. The ribozyme MRE763C is directed against the point mutation [GGT (gly)→CGT (arg) transition], ribozyme MRE764U is directed against [GGT (gly)→GTT (val) transition] (FIG. 1, Panel A). Furthermore, ribozymes against GUC- and GUA -triplets in codon 64 ("RE917"; SEQ ID NO:14), codon 89 ("RE990"; SEQ ID NO:15) and codon 103 ("RE1035"; SEQ ID NO:16) of the wild-type N-ras mRNA were investigated (FIG. 1, Panel B).

In one investigation, short synthetic oligoribonucleotides of 15 nucleotides chain length served as substrates. Cleavage kinetics of all ribozymes were carried out under Michaelis-Menten conditions. The resulting $K_m$ and $k_{cat}$ values are shown in Table IA. The analysis of the kinetic data listed in Table IA reveals equal $k_{cat}/K_m$ values for the ribozymes MRE763C, MRE764U and RE917 of about $0.2 \times 10^6 s^{-1} \times M^{-1}$, whereas ribozyme RE990 possesses much less catalytic efficiency. Binding of the ribozyme MRE763C to its synthetic substrate is determined by measuring the melting temperature ($T_m$). $T_m$ values of approximately 48° C. were obtained for MRE763C- and MRE764U-complexes. Ribozymes RE990 or RE1035 against the wild type mRNA as well as their substrate complexes on the other hand reveal $T_m$ values of approximately 52° C.

In a further investigation, RNA containing the mutant or wild type N-ras sequence from transcription initiation site to termination site was synthesized by in vitro transcription. In order to achieve efficient mRNA cleavage, the target sequence of the substrate (NUX-triplet, N=A,G,C,U; X=C, A,U) is not allowed to be double-stranded or part of a stable hairpin. The in vitro transcribed RNA served as substrate for five ribozymes mentioned above. The catalytic efficiency was examined under "single-turnover" conditions to detect the splice products.

To demonstrate the specificity of ribozyme MRE763C, the cleavage reaction was followed by polyacrylamide gel electrophoresis. Both resulting cleavage products of the mRNA showed the expected size. Table IIA depicts the kinetic properties of the ribozymes under "single-turnover" conditions. Although binding affinity for both the synthetic short substrate and the long transcribed substrate are about the same, as reflected by similar $K_m$ values, the transcribed substrate mRNA is spliced at much slower rate than the short synthetic substrates. See Tables IA and IIA. It was also found that the ribozymes MRE763C or MRE764U, directed against mutant mRNA, do not cleave wild type N-ras mRNA. Therefore, the new ribozymes are able to inhibit the expression of the N-ras oncogene without influencing the expression of the N-ras proto-oncogene. According to the $k_{cat}/K_m$ values, the most effective ribozymes (MRE763C, MRE764U and RE917) were chosen for further investigations with different chemical modifications.

To prevent degradation by RNases, ribozymes were stabilized by modification of the 2'-position of the ribose with different groups. The new ribozymes were characterized by mass spectra (MALDI). Their catalytic properties and stability in cell culture supernatant were determined. 2'-Modifications in the oligoribonucleotides such as 2'-O-methyoxyethoxy-2'-desoxyuridine/cytidine, "EtOMeU"/ "EtOMeC"), 2'-desoxyuridine/cytidine ("dU"/"dC"), 2'-fluoro- 2'-desoxyuridine/cytidine ("FU"/"FC") were combined with additional modifications such as terminal phosphorothioate linkages. See Table IV.

Ribozyme stability was examined in cell culture media up to a time range of about 120 hours. Aliquots were taken at different times, loaded onto a gel and degradation bands could be detected by silver staining. The unmodified ribozyme was digested within half a minute. Introduction of the terminal phosphorothioate linkages at the 3'- and 5'-site ("S") resulted in a half-life time of 2–3 minutes. Further modifications (e.g., 2'-fluoro-2'-desoxyuridine) leads to an increase of stability of approximately 10 minutes. Complete substitution of all pyrimidine nucleotides (e.g., 2'-fluoro-2'-desoxycytidine) produces ribozymes which are stable for about 80 hours.

The cleavage kinetics of the modified ribozymes were performed under "single-turnover" conditions with the in vitro transcribed mRNA. The results are shown in Table III. Introduction of the three 3'- and one 5'-terminal phosphorothioate groups resulted in a slight loss of catalytic efficiency. The catalytic potential of the chemically-modified ribozymes depends on the type of chemical modification, and especially on the type of substitution of the 2'-hydroxy group of the ribose moiety. Although the catalytic activity of the modified ribozymes against codon 13 is lowered to a certain extent in the in vitro cleavage assay as compared to the unmodified analogs, their overall biological activity to inhibit N-ras expression in cell culture or in vivo is much higher due to their enhanced stability against degrading nucleases.

To investigate the inhibitory effect of the modified ribozymes in cell culture, a HeLa cell line containing the N-ras gene fused to a luciferase reporter gene was used. See Example 8. At a 10 µM extracellular concentration of the modified ribozymes MRE763C(FU,FC) or MRE764U(FU, FC), a reduction by 43–61% of expression of the N-ras-luciferase fusion gene could be obtained. See Tables V and VI. The effective dose could be lowered by 10 to 100-fold using uptake enhancers such as lipofectamine(R) or celifectin(R) (Fa. Life Technologies, Eggenstein; Germany), or by using liposomal, microparticle or nanoparticle formulations. Ribozymes containing the active hammerhead-structure, but which were not directed against N-ras mRNA (nonsense controls), did not reduce the expression of N-ras-luciferase fusion.

The present invention also relates to the use of enzymatic RNA molecules as pharmaceuticals. These pharmaceuticals can be used, for example, in the form of pharmaceutical products which can be administered orally, for example, as tablets, coated tablets, hard or soft agar gelatin capsules, solutions, emulsions or suspensions. Inclusion of pharmaceuticals into liposomes, which optionally contain further components such as proteins or peptides, is likewise a suitable administration form. Nano- and micro-particles are also a preferred route of application. They also can be administered rectally, for example, in the form of suppositories, or parenterally, e.g., in the form of injection solutions. Alternative administration forms are topical applications, local applications, for example in form of injections. Nasal administration is also a preferred way of application.

Suitable modes of administration of enzymatic RNA molecules can be determined by those of skill in the art. See, for example, REMINGTON'S PHARMACEUTICAL SCIENCES, 18th Ed. (Mack Publishing Co. 1990), GOODMAN AND GILMAN'S THE PHARMACOLOGICAL BASIS OF THERAPEUTICS, 7th Ed. (MacMillan Publishing Co. 1985), and Ansel et al., PHARMACEUTICAL DOSAGE FORMS AND DRUG DELIVERY SYSTEMS, Fifth Edition (Lea & Febiger 1990).

The type of administration depends on the type of cancer to be treated. The present invention relates to the treatment of diseases which are caused or associated with N-ras expression, especially of codon 13 mutant N-ras expression. N-ras specific ribozymes can for example be used to treat neuroblastoma, melanoma, acute myeloblastic leukaemia (AML), chronic myelogenous leukaemia (CML), multiple myeloma, thyroid tumors, lymphoid disorders and liver carcinoma. For most types of cancer, such as the different types of leukemia, systemic treatment is preferred.

In general, the dosage of administered enzymatic RNA molecule will vary depending upon such factors as the patient's age, weight, height, sex, general medical condition and previous medical history. Typically, it is desirable to provide the recipient with a dosage of enzymatic RNA molecules that results in a blood concentration of from about 10 nanomolar to about 50 micromolar, although a lower or higher dosage also may be administered as circumstances dictate. Preferably, the administered enzymatic RNA molecules achieves a blood concentration of about 0.5 micromolar to about 20 micromolar.

Enzymatic RNA molecules of the present invention can be formulated according to known methods to prepare pharmaceutically useful compositions, whereby enzymatic RNA molecules are combined in a mixture with a pharmaceutically acceptable vehicle. A composition is said to be a "pharmaceutically acceptable vehicle" if its administration can be tolerated by a recipient patient. Sterile phosphate-buffered saline is one example of a pharmaceutically acceptable vehicle. As discussed above, preferred vehicles include liposomes, immuno liposomes, microparticles and nanoparticles. Other suitable vehicles are well-known to those in the art. See, for example, REMINGTON'S PHARMACEUTICAL SCIENCES, 18th Ed. (1990).

For purposes of therapy, enzymatic RNA molecules and a pharmaceutically acceptable vehicle are administered to a patient in a therapeutically effective amount. A combination of an enzymatic RNA molecule and a pharmaceutically acceptable vehicle is said to be administered in a "therapeutically effective amount" if the amount administered is physiologically significant. An agent is physiologically significant if its presence results in a detectable change in the physiology of a recipient patient. In the present context, an agent is physiologically significant if its presence results in an inhibition of tumor growth or a decrease in symptomology associated with a disease caused by or associated with N-ras expression.

The invention is now described by examples which should not be understood as a limitation of the scope of the invention.

EXAMPLE 1

Chemical Synthesis of Ribozymes

Oligoribonucleotides were prepared on an Applied Biosystems 380B DNA Synthesizer on a one μmol scale. Ribonucleotide phosphoramidites and control pore glass columns were obtained from PerSeptive Biosystems®. The first 5'- and the last three 3'-ribonucleosides were stabilized by phosphorothioate. Cytosine- and uracil-ribonucleotides were replaced by the respective 2'-fluoro-, 2'-O-methyl- and 2'-desoxy-modified ribonucleotides. The oligoribonucleotides were base-deprotected by incubation of the glass-support with 3 ml of aqueous concentrated ammonia/ethanol (3:1 (v/v)) at 55° C. for 16 hours. After complete removal of the solvent by SPEED-VAC evaporation, the 2'-silylgroup was removed by overnight incubation at room temperature in 1 M tetrabutylammonium fluoride in tetrahydrofuran. After addition of 0.5 ml of 3 M NaOAc-solution (pH 5.2), the tetrahydrofuran was removed on a SPEED-VAC concentrator and extracted twice with 1 ml of ethylacetate. The oligoribonucleotide was precipitated by addition of 2.5 volumes of absolute ethanol. The RNA was centrifuged at 13,000 U/min and the pellet was dissolved in 1 ml of water. The solution was checked for complete RNA by UV absorption at 260 nm. The RNA solution was purified on denaturing 12% or 20% polyacrylamide gels containing 8 M urea. UV-detected RNA was cut out, and subsequently the referring gel pieces were eluated in 0.05 M NH$_4$OAc-solution (pH 7.0) overnight. The RNA solution was loaded onto a SEPHADEX-G25 column. Fractions of 1 ml were collected and the solutions stored frozen at −20° C. The homogeneity of the ribozyme RNA and substrate RNA were checked by mass spectrometry and analytical PAGE of the 5'-$^{32}$P-labeled oligoribonucleotides followed by autoradiography. RNA concentration was determined by assuming an extinction coefficient at 260 nm of 6.6×10$^3$ M cm$^{-1}$.

EXAMPLE 2

Plasmid Constructions

The pcN1 plasmid (A. Hall. MRC Laboratory for Molecular Cell Biology, London) contained the N-ras gene. Wild type N-ras clones were PCR-amplified using the primers 5'-AGTGCGGATCCTAAATCTGTCCAAAGCAGAGGCAGT-3' (forward primer, SEQ ID NO:3) and 5'-CCGGAATTCTTACATCACCACACATGGCAATCC-3' (reverse primer, SEQ ID NO:4). Restriction endonuclease sites were engineered into the 5'-regions of these primers (reverse primer: EcoRI; forward primer: BamHI). The 629 bp PCR product containing the N-ras gene product was gel-purified, digested with BamHI and EcoRI restriction endonucleases, and ethanol-precipitated prior to cloning. See the cloning strategy outlined in FIG. 2. In a two-part ligation, the N-ras PCR product was cloned into the multiple cloning site of the PBLUESCRIPT II KS transcription vector with the restriction enzymes BamHI and EcoRI. The resulting plasmid was named pMS1-NRAS.

In order to predict the secondary structure of the N-ras mRNA, a 200 bp fragment was cloned at the 5' translation initiation site. For this purpose, four oligodesoxynucleotides with a length of 99–102 nucleotides containing restriction endonuclease sites Xbal and BamHI were synthesized:

```
Oligo 1 (sense):                   (SEQ ID NO:5)
5'-CTAGAGAAACGTCCCGTGTGGGAGGGGCGGGTCTGGGTGCGGCT

GCCGCATGACTCGTGGTTCGGAGGCCCACGTGGCCGGGGCGGGGAC

TCAGGCGCCT-3';

Oligo 1 (antisense):               (SEQ ID NO:6)
5'-GCTGCCAGGCGCCTGAGTCCCCGCCCCGGCCACGTGGGCCTCCG

AACCACGAGTCATGCGGCAGCCGCACCCAGACCCGCCCCTCCCACA

CGGGACGTTTCT-3';

Oligo 2 (sense):                   (SEQ ID NO:7)
5'-GGCAGCCGACTGATTACGTAGCGGGCGGGCCGGAAGTGCCGCT

CCTTGGTGGGGCTGTTCATGGCGGTTCCGGGGTCTCCAACATTTTT

CCCGGTCTGG-3'; and

Oligo 2 (antisense):               (SEQ ID NO:8)
5'-GATCCCAGACCGGGAAAAATGTTGGAGACCCCGGAACCGCCATG

AACAGCCCCCACCAAGGAGCGGCACTTCCGGCCCCGCCCGCTACGT

AATCAGTCG-3'.
```

The oligodesoxynucleotides were hybridized were hybridized and subcloned into the multiple cloning site of PBLUESCRIPT KS II vector using the restriction enzymes Xbal and BamHI. The resulting plasmid was named pMS2-NRAS.

The plasmid pMS5-NRAS, containing the N-ras sequence from transcription initiation site to termination site, was obtained by three-part ligations in which the subcloned PCR product was ligated with the synthetic gene fragment at BamHI and cloned into the PBLUESCRIPT II KS (+/−) vector with the restriction enzymes XbaI and EcoRI. The correct sequence was confirmed by DNA sequence analysis employing standard procedures. Transcription of pMS5-NRAS yielded a RNA of the expected length of about 900 nucleotides.

PCR technology was employed to construct two N-ras activated oncogenes (first plasmid: codon 13 GGT→GTT and second plasmid: codon 13 GGT→CGT) applying two inner primer pairs: 5'-GCAGGTGTTGTTGGGAAAAGCGCACTG-3' (forward primer, SEQ ID NO:9); 5'-CAACAACACCTGCTCCAACCACCAC-3' (reverse primer engineered the first mutation, SEQ ID NO:10) and 5'-GCAGGTCGTGTTGGGAAAAGCGCACTG-3' (forward primer, SEQ ID NO::11); 5'-CCCAACACGACCTGCTCCAACCACCAC-3' (reverse primer engineered the second mutation, SEQ ID NO:12). For amplification of the complete fragment, two outer primer 5'-AGTGCTCTAGAGAAACGTCCCGTGTGGGAGGGGCG-3' (forward primer, SEQ ID NO:13) and 5'-CCGGAATTCTTACATCACCACACATGGCAATCC-3' (reverse primer, SEQ ID NO:4) were used. The extended PCR products were gel-purified, digested with restriction enzymes XbaI and EcoRI, and ethanol-precipitated prior to cloning. Subsequently, each of the two PCR products were cloned into the multiple cloning site of the PBLUESCRIPT II KS vector with the restriction enzymes XbaI and EcoRI. The following plasmids were named pMS5A-NRAS (which contains the first mutation GGT→GTT) and pMS5B-NRAS (which contains the second mutation GGT→CGT). Subsequent sequence analysis confirmed successful insertion of the above mutations.

EXAMPLE 3

In Vitro Transcription

For in vitro transcription, pMS5-NRAS, pMS5A-NRAS and pMS5B-NRAS were linearized by EcoRI digestion, phenol-extracted and ethanol-precipitated. Transcription was carried out in a 100 µl mixture containing 50 ng/µl linearized plasmid DNA, 10 mM DTT, 40 mM Tris-Cl (pH 7.5), 50 mM NaCl, 8 mM $MgCl_2$, 2 mM spermidine, 500 µM rNTP's, 0.8 U/µl RNAse-Inhibitor, 2 µCi/µl [α-$^{32}$P]-ATP and 2.5 U/µl T7 RNA Polymerase. A one-hour incubation at 37° C. was followed by the addition of 25 Units of DNAseI, and the mixture was incubated for an additional 30 min at 37° C. After subsequent phenol extraction, the aqueous phase was transferred into a CENTRICON-100 tube and centrifuged at 3,400 U/min for 30 min. The RNA-solution was checked for homogeneity by UV absorption and 6% analytical PAGE (8 M urea). The solution was stored frozen at −20° C.

EXAMPLE 4

Kinetics with Synthetic Substrates

Kinetic constants $K_m$ and $k_{cat}$ were determined from Eadie-Hofstee plots carried out with 5'-$^{32}$P-labeled substrate. The RNA substrate was labeled by reaction with T4 polynucleotide kinase and [γ-$^{32}$P]-ATP. 5'-end labeled substrate was purified from [γ-$^{32}$P]-ATP with CENTRICON-3 tubes. Ribozyme and substrate were heated separately for 1 min at 75° C. in 50 mM Tris-Cl (pH 7.5). After cooling to 37° C. for 5 min, 100 mM $MgCl_2$ were added to a final concentration of 10 mM, and the solution was incubated for an additional 5 min at 37° C. Multiple turnover reactions were carried out in a volume of 100 µl with concentrations of substrate between 20–500 nM and ribozyme concentrations from 2 to 5 nM in 50 mM Tris-Cl (pH 7.5) and 10 mM $MgCl_2$ at 37° C. Reactions were initiated by addition of ribozyme. The reaction was stopped by mixing the ribozymes with an equal volume of stop solution (8 M urea, 25 mM EDTA). The cleavage reactions were analyzed on 20% denaturing polyacrylamide gels (8 M urea) and scanned on a Molecular Dynamic Phosphorimaging system.

TABLE IA

| Ribozyme | $k_{cat}$ [$s^{-1}$] | $K_m$ [nM] | $k_{cat}/K_m$ [$10^6 \times s^{-1} \times M^{-1}$] |
|---|---|---|---|
| RE917 | 0.013 | 78 | 0.2 |
| RE990 | 0.004 | 404 | 0.009 |
| RE1035 | 0.013 | 277 | 0.05 |
| MRE763C | 0.015 | 82 | 0.2 |
| MRE764U | 0.012 | 65 | 0.2 |

$K_m$ and $k_{cat}$ values of ribozymes with synthetic substrates. The $k_{cat}$ and $K_m$ values were determined under Michaelis-Menten conditions as described in Example 4.

TABLE IB

| Modifications of MRE763C | $k_{cat}$ [$min^{-1}$] | $K_m$ [nM] | $k_{cat}/K_m$ [$min^{-1} nM^{-1}$] | $k_{cat}/K_m$ (relative) |
|---|---|---|---|---|
| None | 3.760 | 72 | 0.05100 | 1 |
| EtOMeU, EtOMeC, $U_4U_7$–$NH_2$ | 0.530 | 22 | 0.02400 | 0.470 |
| FU, FC, $U_4U_7$–$NH_2$ | 0.300 | 16 | 0.01900 | 0.380 |
| S, EtOMeU, EtOMeC, $U_4U_7$–$NH_2$ | 0.220 | 18 | 0.01200 | 0.230 |
| EtOMeU, EtOMeC | 0.027 | 105 | 0.00026 | 0.005 |

EXAMPLE 5

Kinetics with In Vitro Transcribed RNA

The cleavage efficiency under "single-turnover" conditions was determined in a volume of 10 µl using 20–1200 nM ribozyme, 50 mM Tris-Cl (pH 7.5) and 10 mM $MgCl_2$. The reaction was initiated by addition of RNA substrate to a final concentration of 10 nM substrate over 1 h at 37° C. The reaction was stopped by mixing 8 µl of stop solution to each reaction. The reaction was analyzed on 6% denaturing polyacrylamide gels and scanned on a Molecular Dynamics Phosphor Imager. The single turnover $k_{cat}/K_m$ values were determined as described by Heidenreich et al., *J. Biol. Chem.* 267:1904 (1992).

TABLE IIA

| Ribozyme | $k_{cat}$ [$10^6 \times s^{-1}$] | $K_m$ [nM] | $k_{cat}/K_m$ [$s^{-1} \times M^{-1}$] |
|---|---|---|---|
| RE917 | 59 | 63 | 938 |
| RE990 | 72 | 234 | 307 |
| RE1035 | 44 | 425 | 103 |
| MRE763C | 266 | 71 | 3752 |
| MRE764U | 137 | 113 | 1212 |

$K_m$ and $k_{cat}$ values of several ribozymes with transcribed N-ras mRNA as substrate. The catalytic values are determined under "single-turnover" conditions as described in Example 5.

TABLE IIB

| Ribozyme Modifications | $k_{react}$ [$10^6 s^{-1}$] | $K_m$ [nM] | $k_{react}/K_m$ [$s^{-1} M^{-1}$] | $k_{react}/K_m$ (relative) |
|---|---|---|---|---|
| RE917 | 59 | 63 | 938 | 1 |
| S | 88 | 120 | 733 | 0.78 |
| S, FU | 60 | 400 | 150 | 0.16 |
| S, dU, dC | 20 | 1420 | 14 | 0.015 |
| FU, FC | 66 | 202 | 326 | 0.35 |
| MRE764U | 137 | 113 | 1212 | 1 |
| FU, FC | 62 | 120 | 516 | 0.42 |

TABLE IIC

| Modifications of Ribozyme MRE763C | $k_{react}$ [$10^{-6} s^{-1}$] | $K_m$ [nM] | $k_{react}/K_m$ [$s^{-1} M^{-1}$] | $k_{react}/K_m$ (relative) |
|---|---|---|---|---|
| None | 266 | 71 | 3748 | 1 |
| FU, FC | 50 | 39 | 1266 | 0.340 |
| FU, FC, $U_4U_7$–$NH_2$ | 173 | 71 | 2437 | 0.650 |
| EtOMeU, EtOMeC, $U_4U_7$–OH | 147 | 51 | 2882 | 0.770 |
| EtOMeU, EtOMeC, $U_4U_7$–$NH_2$ | 173 | 73 | 2370 | 0.630 |
| EtOMeU, EtOMeC, $U_4U_7$–F | 39 | 135 | 288 | 0.077 |
| S, FU, FC | 51 | 44 | 1159 | 0.300 |
| S, EtOMeU, EtOMeC, $U_4U_7$–$NH_2$ | 27 | 190 | 142 | 0.038 |

TABLE III

| Ribozyme | $k_{cat}$ [$10^6 \times s^{-1}$] | $K_m$ [nM] | $k_{cat}/K_m$ [$s^{-1} \times M^{-1}$] |
|---|---|---|---|
| RE917 | 59 | 63 | 938 |
| RE917 (thioat) | 88 | 120 | 733 |
| RE917 (thioat, FU) | 60 | 400 | 150 |
| RE917 (FU, FC) | 66 | 202 | 326 |
| RE917 (thioat, dU, dC) | 20 | 1420 | 14 |
| MRE763C | 266 | 71 | 3752 |
| MRE763C (thioat, FU, OMeU$_4$U$_7$) | 53 | 61 | 869 |
| MRE763C (thioat, FU, FC) | 51 | 44 | 1159 |
| MRE763C (FU, FC) | 50 | 39 | 1266 |
| MRE764U | 137 | 113 | 1212 |
| MRE764U (FU, FC) | 62 | 120 | 516 |

$k_{cat}$ and $K_m$ values of different modified ribozymes with transcribed N-ras mRNA. Reactions conditions were as described in Example 5.

EXAMPLE 6

Analysis of Stability of Ribozymes

NIH3T3-cells were maintained as a monolayer in Dulbecco's modified Eagle's medium supplemented with 10% heat-inactivated FCS and 100 Units/ml penicillin. After attaining a cell density of $2 \times 10^6$ cells/ml, the supernatant was removed from the cells. Ribozyme solutions (32 µl) containing different modified ribozymes were added to the cell culture supernatant (525 µl) to reach a final ribozyme concentration of 5 µM. Aliquots (67 µl) were taken at different times and transferred to liquid nitrogen to stop nuclease activity. After SPEED-VAC evaporation, the pellets were resuspended in formamide. The different aliquots were analyzed in 20% polyacrylamide gels (8 M urea) followed by silver staining.

TABLE IV

| Ribozyme | Stability in Supernatant of Cell Cultures (half-life-times) |
|---|---|
| Unmodified | 0.5 min |
| S | 3.0 min |
| S, FU | 10.0 min |
| FU, FC | 50 h |
| FU, FC, $U_4U_7$–$NH_2$ | 50 h |
| S, FU, OMeC | 80 h |
| S, OMeU, OMeC | 80 h |
| S, dU, dC | 80 h |
| S, FU, FC | 80 h |
| EtOMeU, EtOMeC, $U_4U_7$–OH | 30 min |
| EtOMeU, EtOMeC, $U_4U_7$–$NH_2$ | 80 h |
| EtOMeU, EtOMeC, $U_4U_7$–F | 80 h |
| EtOMeU, EtOMeC | 80 h |
| S, EtOMeU, EtOMeC, $U_4U_7$–$NH_2$ | 80 h |
| S, EtOMeU, EtOMeC, $U_4U_7$–F | 80 h |

Stability of chemically modified ribozymes in cell culture supernatant. Reaction conditions were carried out as described in Example 6.

EXAMPLE 7

Melting Curves

UV temperature curves were measured at 260 nm using a Varian Cary-1 UV/VIS-spectrophotometer. The target was prepared by dissolving the ribozyme in a buffer containing 50 mM Tris-Cl (pH 7.5) and 10 mM MgCl$_2$. The sample was transferred in a cuvette with a 10 mm path length. The ribozyme was denatured at 80° C. for 5 min, and subsequently the substrate RNA and substrate DNA were added and the whole mixture was renatured at 1° C./min. Melting curves at 260 nm were performed by heating the solution in the cuvette at 0.75° C./min and acquiring absorbance data every 0.5° C. step until 80° C. was reached. The $T_m$ value and thermodynamic parameters of transition were obtained by fitting data of a two transition state model with the GraFit version 2.0 from Sigma Chemicals Co. software using the method of Marky and Breslauer, *Biopolymers* 26:1601 (1987).

EXAMPLE 8

Inhibition of N-Ras in HeLa Cells

To investigate the inhibitory effect of the ribozymes, an N-ras-luciferase reporter gene was constructed. A 450 bp fragment of the N-ras gene, containing about 80 bp of the 5'-nontranslated sequences, the natural translation initiation codon and the nucleotides coding for 134 amino acid of the mutant or wild type N-ras protein, were fused in frame with the luciferase gene (Photinus pyralis). Luciferase activity (light units) of the N-ras-luciferase fusion protein was measured.

TABLE V

Inhibition of N-Ras-Luciferase Gene Expression by 10 μM MRE763 in HeLa Cells

| Ribozyme | Light Units ($10^5$) | Reduction (%) |
|---|---|---|
| nonsense | 2.58 | 0 |
| MRE763C (FU, FC) | 1.0–1.1 | 57–61 |

TABLE VI

Inhibition of N-Ras-Luciferase Gene Expression by 10 μM MRE764 in HeLa Cells

| Ribozyme | Light Units ($10^5$) | Reduction (%) |
|---|---|---|
| nonsense | 4.4 | 0 |
| MRE764U (FU, FC) | 2.2–2.5 | 43–50 |

EXAMPLE 9

Reduction of N-Ras Expression in NIH3T3 Cells by Cleavage of mRNA with Retrovirally Mediated Ribozymes The wild-type and mutated (codon 13) N-Ras genes differ only in a point mutation involving an amino acid exchange. As a result, protein p21 ras loses the ability to change the cell metabolism, leading to malignant transformation of the cells. In contrast to normal cells, cancer cells are able to grow in serum-free medium. In soft agar (semisolid), the cancer cells group into cell clusters (foci), which are regions in which the cells proliferate at random. The random growth is caused by a loss of contact inhibition of the transformed cells.

The cells of the constitutively N-ras expressing clones 2 and 4 (mutation in codon 13) were subcultured in soft agar using the colony-forming agar assay of Cowley et al., *Cell* 77:841 (1994). The colony-forming agar assay is a semisolid method in which cells are suspended in a 0.3% agar upper layer and plated out over a 0.5% agar lower layer in Petri dishes. The lower layer was prepared by heating a 2.5% solution of agar in deionized water. After cooling the agar to 45° C. in a water bath, an agar mix of 0.5% agar was prepared by combining 25 ml of 1×DMEM medium, 10 ml of 2.5% agar, 10 ml of 2×DMEM medium, and 5 ml of fetal calf serum. One milliliter samples of the agar mix were pipetted into 35 mm Petri culture dishes and stored at 4° C. for 30 minutes.

The upper layer was prepared by adding 0.2 ml of agar mix to 1 ml of about $5 \times 10^4$ cells/ml suspension, and adding DMEM medium to a total volume of 1.7 ml. One milliliter samples were pipette onto bottom agar layers and incubated for 14–21 days at 37° C. Agar preparations in 30 mm culture dishes were placed in 100 mm Petri dishes in groups of two, together with another Petri dish containing only sterile deionized water. The clones were visualized with a microscope and isolated from agar using a pipette. The isolated clones were transferred into 24-well plates and expanded.

In one study, $2.5 \times 10^4$ cells/ml were placed in Petri dishes. The mutated N-ras clones 2 and 4 formed colonies after about 4–6 days in soft agar. NIH3T3 cells and NIH3T3 cells stably transfected with pcDNA3 plasmid (Invitrogen) were seeded out on the soft agar as controls. The two controls were unable to form foci.

To increase the number of transformed cells, the individual colonies of the N-ras constructs were isolated in 24-well plates and expanded. A soft agar assay was carried out again ($2.5 \times 10^4$ cells/ml) with clones 2 and 4 of the mutated N-ras gene. After 4–6 days, more colonies of the transformed cells were discernable, and after 14 days, about 70% of the cells consisted of foci. Even in culture, the cells with the mutated N-ras gene formed colonies of transformed cells. Thus, in the case of NIH3T3 cells, a single oncogene is sufficient to transform the cells into cancer cells. Transition into a malignant transformed phenotype occurred through transfection.

A study was performed to investigate whether ribozyme MRE763C can induce a reversion of the malignant phenotype expressed by N-ras transformed NIH3T3 cells. To this end, virus populations of the established GP+envAm-12 producer cell lines, which constitutively express the active ribozyme MRE763C and the pBabc-Puro plasmid, were used for gene transfer by infection into the target cells, namely NIH3T3 cells constitutively expressing the N-ras mutants (clones 2 and 4).

To obtain a pure cell population expressing the ribozyme or control ribozyme, puromycin selection (1.5 μg/ml) was started after 48 hours. The control ribozyme was a modification of SEQ ID NO:1, in which the tenth nucleotide was an adenine instead of a guanine. After 10 days of selection, three clones from each construct were isolated in 24-well plates and expanded in T25 culture bottles.

One of the three isolated clones and a mixed population of NIH3T3 cells constitutively expressing ribozyme MRE763C and pBabc-Puro (stably transfected with the N-ras mutants [clones 2 and 4]) were subcultured in soft agar and examined using the colony-forming agar assay. These cells and the following controls were plated in Petri dishes at a concentration of $2 \times 10^4$ cells/ml: NIH3T3 cells (negative control), NIH3T3 cells stably transfected with the pcDNA3 plasmid (negative control), and the N-ras mutant clones 2 and 4 that had not been infected with the retroviral constructs pBabc-PuroREC and pBabc-Puro (positive controls). The pBabc-Puro construct is described by Morgenstem et al., *Nucl. Acids Res.* 18:3587 (1990). The pBabc-PuroREC construct expresses the active ribozyme MRE763C.

The soft agar cultures were incubated for 7–14 days at 37° C. and 5% $CO_2$. The reduction in transformed N-ras NIH3T3 cells was analyzed by counting cell clusters under a microscope. The soft agar preparations were set up in quadruplicate for each construct and the mean values were calculated, as presented in Table VII.

TABLE VII

Reduction in Transformed N-Ras NIH3T3 Cells by Ribozymes

| Construct | Number of Clones [mean] Clone 2/Clone 4 | Reduction [%] |
|---|---|---|
| NIH3T3 (negative control) | 3 | |
| NIH3T3 (pcDNA3[1]) (negative control) | 5 | |
| NIH3T3 (pcDNA3-NRASC[2]) (positive control) | 91/102 | 0 |
| NIH3T3 (pcDNA3-NRASC) infected with ribozyme | 42/49 | 54/52 |
| NIH3T3 (pcDNA3-NRASC) infected with pBabc-Puro | 65/60 | 29/41 |

[1]The pcDNA3 construct was obtained from Invitrogen BV.
[2]The pcDNA3-NRASC construct was prepared by cleaving the mutated N-ras gene from pMS5B-NRAS with ApaI and NotI, and inserting the gene into a PcDNA3 vector.

Through transduction with ribozyme, a reversion of the malignant transformed phenotype took place, but this also occurs in the presence of the retroviral vector alone. That is, the ribozyme MRE763C caused a reversion of the malignant phenotype by about 18%.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety. Priority application European application No. 96108326.8, filed May 24, 1996, including the specification, drawings, claims and abstract, is hereby specifically incorporated by reference.

What is claimed is:

1. An enzymatic RNA molecule that cleaves mutant N-ras mRNA, wherein said enzymatic RNA molecule comprises a hammerhead motif that selectively binds codon 13 of said mutant N-ras mRNA, and wherein said mutant N-ras has at least one point mutation in codon 13, and wherein said point mutation generates a NUX cleavage site.

2. The enzymatic RNA molecule of claim 1, wherein said enzymatic RNA molecule comprises the base sequence
5'-CCAACACCUGAUGAGCGUUAGCGAAACCUGC U-3' (SEQ ID NO:1).

3. The enzymatic RNA molecule of claim 1, wherein said enzymatic RNA molecule comprises the base sequence
5'-UCCCAACCUGAUGAGCGUUAGCGAAACACCU G-3' (SEQ ID NO:2).

4. The enzymatic RNA molecule of claim 1, wherein said enzymatic RNA molecule further comprises a chemical modification.

5. The enzymatic RNA molecule of claim 4, wherein said enzymatic RNA molecule comprises at least one chemical modification selected from the group consisting of (1) a modification of at least one of the 2'-hydroxy groups of said enzymatic RNA molecule, (2) a modification of at least one sugar residue in the phosphate/sugar backbone of said enzymatic RNA molecule, (3) a modification of at least one phosphate internucleoside residue of said enzymatic RNA molecule, (4) a replacement of at least one phosphate bridge of said enzymatic RNA molecule with a compound selected from the group consisting of formacetal, 3'-thioformacetal and methylhydroxylamine, (5) a partial substitution of the phosphate/sugar backbone of said enzymatic RNA molecule with polyamide nucleic acid, (6) a modification of at least one of the bases of said enzymatic RNA molecule, and (7) a substitution of at least one end of said enzymatic RNA molecule.

6. The enzymatic RNA molecule of claim 5, wherein said chemical modification is a modification of at least one of the 2'-hydroxy groups of said enzymatic RNA molecule.

7. The enzymatic RNA molecule of claim 6, wherein said 2'-hydroxy modification is selected from the group consisting of 2'-deoxyribo-, 2'-O-methyl-, 2'-fluoro- and 2'-amino-.

8. The enzymatic RNA molecule of claim 5, wherein said chemical modification is a modification of at least one sugar residue in the phosphate/sugar backbone of said enzymatic RNA molecule.

9. The enzymatic RNA molecule of claim 8, wherein said modified sugar is selected from the group consisting of alpha-furanoside, D-furanoside, carbocyclic five-membered ring analogs, ring-expanded sugars, ring-contracted sugars and acyclic sugars.

10. The enzymatic RNA molecule of claim 9, wherein said modified sugar is located in said binding region of said enzymatic RNA molecule.

11. The enzymatic RNA molecule of claim 8, wherein said modified sugar is selected from the group consisting of 2'-O-alkylribose, 2'-fluoro-2'-deoxyribose and 2'-amino-2'-deoxyribose.

12. The enzymatic RNA molecule of claim 11, wherein said 2'-O-alkylribose is selected from the group consisting of 2'-O-methyl, 2'-O-butyl, 2'-O-allyl and 2'-O-methoxyethoxy.

13. The enzymatic RNA molecule of claim 5, wherein said chemical modification is a modification of at least one phosphate internucleoside residue of said enzymatic RNA molecule.

14. The enzymatic RNA molecule of claim 13, wherein said modified phosphate internucleoside residue is selected from the group consisting of phosphorothioate, phosphorodithioate, alkylphosphonate, arylphosphonate, arylalkylphosphoramidate, phosphate ester, 3'-3'-inversion and 5'-5'-inversion.

15. The enzymatic RNA molecule of claim 5, wherein said chemical modification is a replacement of at least one phosphate bridge of said enzymatic RNA molecule with a compound selected from the group consisting of formacetal, 3'-thioformacetal and methylhydroxylamine.

16. The enzymatic RNA molecule of claim 5, wherein said chemical modification is a partial substitution of the phosphate/sugar backbone of said enzymatic RNA molecule with polyamide nucleic acid.

17. The enzymatic RNA molecule of claim 5, wherein said chemical modification is a modification of at least one of the bases of said enzymatic RNA molecule.

18. The enzymatic RNA molecule of claim 17, wherein said modified bases are selected from the group consisting of 5-propynyl-U, 5-propynyl-C, 7-deaza-7-propynyl-A, 7-deaza-7-propynyl-G, 5-methyl-C and 5-fluoro-U.

19. The enzymatic RNA molecule of claim 5, wherein the chemical modification is a substitution of at least one end of said enzymatic RNA molecule, wherein said substituted end is selected from the group consisting of 5'-end, 3'-end and 2'-end.

20. The enzymatic RNA molecule of claim 19, wherein said substituted end comprises a compound selected from the group consisting of lipophilic radical, steroid residue, vitamin E, vitamin A, vitamin D, a conjugate which utilizes natural carrier systems and an end-group with an intercalating moiety which enhances binding to said mutant N-ras mRNA.

21. The enzymatic RNA molecule of claim 20, wherein said lipophilic radical is —O—$(CH_2)_n CH_3$, wherein n is an integer from 6 to 18.

22. The enzymatic RNA molecule of claim 20, wherein said conjugate which utilizes natural carrier systems is selected from the group consisting of bile acid, folic acid, mannose and peptide.

23. The enzymatic RNA molecule of claim 20, wherein said end-group with an intercalating moiety is a psoralene derivative or an acridine derivative.

* * * * *